United States Patent [19]

Richter et al.

[11] Patent Number: 4,773,433
[45] Date of Patent: Sep. 27, 1988

[54] IMPLANTABLE ELECTRODE

[75] Inventors: Gerhard Richter, Erlangen; Erhard Weidlich, Spardorf; Konrad Mund, Erlangen; Horst Böder, Biberach, all of Fed. Rep. of Germany

[73] Assignee: Siemens Aktiengesellschaft, Berlin and Munich, Fed. Rep. of Germany

[21] Appl. No.: 364,268

[22] Filed: Apr. 1, 1982

Related U.S. Application Data

[63] Continuation of Ser. No. 178,601, Aug. 15, 1980, abandoned, which is a continuation of Ser. No. 778,213, Mar. 16, 1977, abandoned.

[30] Foreign Application Priority Data

Mar. 26, 1976 [DE] Fed. Rep. of Germany ....... 2613072

[51] Int. Cl.$^4$ .............................................. A61N 1/05
[52] U.S. Cl. .................................................. 128/784
[58] Field of Search ...................... 128/642, 784–786, 128/419 P

[56] References Cited

U.S. PATENT DOCUMENTS

| 3,722,005 | 3/1973 | Cowland | 128/642 |
| 3,981,309 | 9/1976 | Cannon | 128/419 P |
| 4,011,861 | 3/1977 | Enger | 128/642 |
| 4,033,357 | 7/1977 | Helland et al. | 128/785 |

FOREIGN PATENT DOCUMENTS 1219017  1/1971  United Kingdom ............ 128/419 P

OTHER PUBLICATIONS

Kadefors et al, "A Percutaneous Electrode . . . ", Med. & Biol. Eng., vol. 8, No. 2, pp. 129–135, 1970.

Primary Examiner—Lee S. Cohen
Attorney, Agent, or Firm—Kenyon & Kenyon

[57]  ABSTRACT

An implantable electrode, particularly a stimulation electrode, in which the electrode head consists of vitreous carbon which is preferably surface activated.

6 Claims, 1 Drawing Sheet

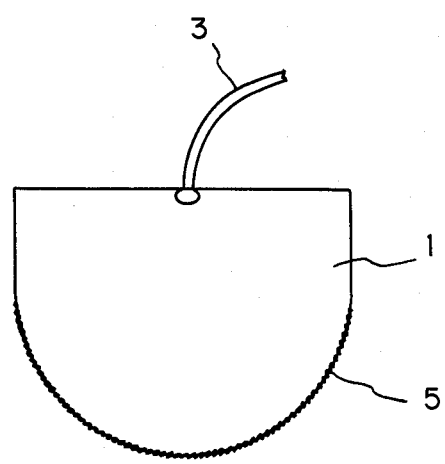

4,773,433

IMPLANTABLE ELECTRODE

This is a continuation, of application Ser. No. 178,601 filed Aug. 15, 1980, now abandoned, which in turn is a continuation of application Ser. No. 778,213, filed Mar. 16, 1977, now abandoned.

BACKGROUND OF THE INVENTION

This invention relates to implantable electrodes in general and more particularly an improved implantable electrode particularly useful as a stimulation electrode, as well as its application.

Stimulation or stimulating electrodes, for instance, for heart pacemakers generally include an insulated cable lead and an electrode head for transmitting the stimulation pulses. The electric stimulation of the heart when the propagation of the stimulation is interrupted presupposes the generation of a certain electric field strength at an excitable cell membrane. After the stimulation is triggered, the latter propagates automatically over the entire heart muscle and causes the heart to contract.

To trigger the stimulus an electronic pacemaker which consists of an implantable electronics part having a power supply unit and a stimulation circuit including the stimulating electrode and an indifferent electrode is used. During the stimulation pulse a small capacitor is partially discharged through the stimulation circuit within 0.5 to 2 msec. In the intervals between the pulses, the capacitor is recharged from the power supply unit, i.e., a battery. During the pulse, the field strength required for triggering of the stimulus exists in the excitable tissue in the vicinity of the stimulation electrode.

Heretofore it has been customary to use stimulation electrodes of platinum or Elgiloy. However, these electrodes have the disadvantage of causing the adjacent tissue to degenerate, since they surround themselves with a connecting or connective tissue layer about 0.5 to 1 mm thick which is not excitable. This connective tissue layer develops over a period of approximately 3 to 4 weeks. During this time, the stimulation threshold continuously increases, i.e., an increasingly larger current is required for triggering the stimulation process. Thus, the voltage required also increases. The excitable tissue, so to speak, moves away from the electrode, and more energy must therefore by supplied to generate the same field strength at the surface of the virtual electrode formed in this manner as at the stimulation electrode itself. If the head of the stimulation electrode consists, for instance, of an hemisphere with a radius of 1 mm and a connecting tissue layer about 1 mm thick develops around this stimulation electrode, then the stimulation threshold current increases fourfold. Since the voltage increases approximately at the same rate, the power required becomes about 16 times as large. This means that the requirements placed on the capacity and the voltage of the energy source depend to a considerable degree on the tissue growth at the stimulating electrode.

Although it is known to use as electrode materials for stimulation electrodes spectrally pure graphite and carbon, such electrodes nevertheless have not found acceptance in practice. For, at the surface of these electrodes, at thin capsule of connective tissue also develops, and in addition, these electrodes do not withstand the mechanical stresses in the heart. In fact, the wear and the danger of breakage are so great, that they are not suited in the long run for human implantation.

SUMMARY OF THE INVENTION

It is an object of the present invention to develop an implantable electrode which uses as little energy as possible even in long term operation but which at the same time has high mechanical stability.

According to the present invention, this is achieved with an electrode head which consists of vitreous carbon, i.e. glassy carbon.

Vitreous carbon, also called glass-like carbon, is obtained by carbonizing three-dimensionally cross-linked synthetic resins such as phenolformaldehyde or furane resins. The glass-like carbon structures produced in this process are microcrystalline and exhibit only exemely small zones of graphite-like layers. Implantable electrodes with an electrode head of vitreous carbon are extremely strong mechanically, since vitreous carbon is very hard and shows no wear. Furthermore, its surface is smooth like glass and is thereby particularly tissue compatible, so that hardly any capsulation through the formation of connecting tissue occurs in the tissue where it is used as the electrode material.

It is particularly advantageous, with the implantable electrode according to the invention, if the electrode head of vitreous carbon is surface-activated. Within the scope of the present specification, an activated surface is understood to mean a surface with a microporous structure, i.e., a roughened surface.

The activation of the electrode head of vitreous carbon is generally performed by oxidants such as oxidizing acids, e.g., nitric acid. Electrochemical oxidation is also an effective activation method. However, vitreous carbon which was heat treated in an oxidizing atmosphere, the activating taking place preferably by heating in air to temperatures above 400° C. is used to particular advantage. With such treatment, a slight burning off of the surface which has an extremely advantageous effect on the electrical properties occurs. The activation can also be accomplished by heating in an oxygen, water vapor or carbon dioxide atmosphere, the activating time, as in the case of heating in air, being preferably less than 1 hour at a temperature of 400° to 800° C.

The roughening of the electrode surface, with the smooth surface being maintained macroscopically, can also be performed at the time when the electrode is being prepared. For this purpose, a blank of synthetic resin, from which the electrode head is to be made, is immersed prior to the pyrolysis in a concentrated solution of polyacrylic nitril in zinc chloride. In this manner, a very thin layer of microporous carbon with pores having a diameter in the range of about 5 Å is produced on the electrode head in the carbonizing.

By activating the vitreous carbon, the polarization losses which occur at the boundary surface between the electrode and the tissue and do not contribute to an increase of the field strength in the adjacent excitable tissue, can be kept very low. In this manner, little capsulation through connecting tissue formation as well as low energy consumption and, along therewith, good continuous operation behavior are ensured with the implantable electrode according to the present invention, since the current density of the stimulation threshold is not increased for the duration of the implantation.

Because of the smooth, glass-like surface of the vitreous carbon, there might be danger, with the implantable electrode according to the invention that there is not enough adhesion to the body tissue. Since the surface scarcely presents points of attack for the tissue to grow on the electrode might have a tendency to dislocate, so that reliable, continuous stimulation would not be assured. In order to fix the electrode securely, therefore, a suitable holder at the cable lead in the immediate vicinity of the electrode head can be provided. However, to reliably fix the implantable electrode according to the invention the electrode head itself can also be used. To accomplish this, the vitreous carbon is provided with slots or holes, i.e. pores in the range of about between 50 to 500 μm into which the tissue can grow. Since it is difficult to work such a structure into the finished electrode head of vitreous carbon, it is advantageous to form it in the blank before the head is made. For this purposes, formed bodies or fibers can be embedded in the blank. These are decomposed or evaporated in the pyrolysis, with only a corresponding hole or slot structure remaining. Zinc or polyethyhlene can be used, for instance, for embedding.

DESCRIPTION OF THE FIGURE

The FIGURE is a cross-sectional view of the implantable electrode of this application wherein (1) is a schematic representation of the electrode head, (3) is the electrode lead, and (5) is illustrative of a microporous surface (not shown to scale).

DETAILED DESCRIPTION OF THE INVENTION

To determine the suitability of the implantable electrode according to the invention as a stimulation electrode, several electrodes were implanted in the thighs of cats.

An electrode with an hemispherical electrode head (surface: 0.08 cm$^2$) of vitreous carbon which is not pre-treated initially shows a stimulus threshold voltage of 0.46 V at a current of 0.17 mA. During an implantation period of 30 days, these values remain constant within the measuring accuracy. The stimulus threshold is divided into an ohmic loss at the body resistance (800 to 1000 ohms) and into a polarization loss, which occurs predominantly at the stimulation electrode. The polarization losses are about one-half to two-thirds of the total losses. With a voltage of 5 V, as is required in conventional heart pacemakers, development of gas would accordingly come about at the stimulation electode, since the polarization is about 2 to 3 V and would therefore be above the decompositon voltage of water. Therefore, difficulties would occur with the secure fixation of the stimulation electrode in the body. Due to the fact that, with the implantable electrode according to the invention, only a slight increase in the stimulus threshold possibly occurs, however, only a voltage of about 1 to 2 V is still needed if it is used for a heart pacemaker. The decomposition voltage of water is thus not reached here any more.

A stimulation electrode with an electrode head of superficially activated vitreous carbon was prepared in such a manner that the electrode head was first worked with emory paper and was subsequently annealed at about 500° C. in a quartz tube in air for about half an hour in a sintering slide. A silver wire, which was cemented to the electrode, served as the contact, as in the case of the stimulation electrode with vitreous carbon which was not pre-treated. The electrode likewise had an hemispherical electrode head with a surface of 0.08 cm$^2$.

Immediately after implantation, this stimulation electrode had a stimulus current of 0.15 mA. After four weeks, the stimulus current was 0.16 mA. The stimulus voltage was, in each case, 0.11 V. The stimulus threshold therefore remained unchanged for the duration of the implantation.

In comparison thereto, a commercially available platinum-iridium stimulation electrode while initially also displaying a stimulus threshold current of 0.15 mA, had this value increase to 0.42 mA after 30 days. At the same time, the stimulus threshold voltage increased from an initial value of 0.165 V to 0.45 V. During the implantation period, a connecting tissue layer 0.6 mm thick had developed.

The increase of the stimulus threshold, however, in this case is explained not by the growth of the connecting tissue alone, as was determined by the following comparison test. In a porous platinum stimulation electrode, which was obtained by sintering powdered platinum black at 1450° C., the stimulus threshold rose within 33 days from 0.20 mA to 0.39 mA, while the connecting tissue layer formed in this period was only 0.2 mm thick. For such a rise of the stimulus threshold, the connecting tissue layer should have had a thickness of 0.5 to 0.6 mm, however. The reason for this fact would seem to be that the muscle cells in the vicinity of the electrode are damaged even before they have completely degenerated into connecting tissue; this damage manifests itself in an increased stimulus threshold. Corresponding damage evidently does not occur in electrodes with an electrode head of vitreous carbon, however, as is concluded from the unchanged stimulus threshold.

The experimental results show that implantable electrodes with an electrode head of superficially activated vitreous carbon show little polarization and are therefore suited to a particularly high degree as stimulation electrodes for heart pacemakers. For, since due to the small increase in the stimulation threshold little energy is consumed for the stimulation mechanism, the life of the current source is long and the latter can also be made small. Further, the electrodes are surrounded only be a very thin connecting tissue skin, so that the electrode head can be made still smaller without more polarization occuring. In this manner, the energy consumption is reduced further.

In addition to its use as a stimulation electrode for heart pacemakers, the implantable electrode according to the present invention can also be used as a stimulation electrode for muscle and nerve stimulation. Furthermore, this electrode can also be used for the measurement of oxygen in the body.

What is claimed is:

1. A tissue-implantable electrode, particularly a stimulating electrode, including an electrode head and an electrical lead connected thereto, the head consisting of a vitreous carbon body superficially activated by an oxidizing treatment, said treatment forming a thin, macroscopically-smooth surface layer of carbon having a microporous structure, whereby polarization losses which occur at the boundary surface between the electrode and the tissue are kept low, and the stimulation threshold voltage remains substantially constant over the duration of the implantation.

2. The electrode of claim 1 wherein the surface layer has a pore diameter of about 5 Angstroms.

3. The electrode of claim 1 wherein the surface layer is formed by heating said vitreous carbon body in an oxidizing atmosphere.

4. The electrode of claim 3 wherein the vitreous carbon body is heated in air at about 400°–800° C.

5. The electrode according to claim 3 wherein the vitreous carbon body is heated in air at a temperature above about 400° C.

6. The electrode of claim 1 wherein the vitreous carbon body further comprises about 50–500 μm pores adapted to adhere said electrode to said tissue.

* * * * *